United States Patent
Takewaki et al.

(10) Patent No.: US 6,835,369 B2
(45) Date of Patent: Dec. 28, 2004

(54) MOLECULAR SIEVE CIT-6

(75) Inventors: Takahiko Takewaki, Kawasaki (JP); Mark E. Davis, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 149 days.

(21) Appl. No.: 10/307,690

(22) Filed: Dec. 2, 2002

(65) Prior Publication Data

US 2003/0127359 A1 Jul. 10, 2003
US 2004/0200757 A9 Jul. 10, 2003

Related U.S. Application Data

(60) Division of application No. 09/626,650, filed on Jul. 27, 2000, now Pat. No. 6,521,206, which is a division of application No. 09/288,247, filed on Apr. 8, 1999, now Pat. No. 6,117,411, which is a continuation-in-part of application No. 09/106,598, filed on Jun. 29, 1998, now abandoned.

(51) Int. Cl.$^7$ ............................................... C01B 39/02
(52) U.S. Cl. ..................... 423/705; 423/712; 423/716; 423/DIG. 27
(58) Field of Search ................................. 423/705, 712, 423/716, DIG. 27

(56) References Cited

U.S. PATENT DOCUMENTS

| | | | | |
|---|---|---|---|---|
| RE28,314 E | * | 1/1975 | Wadlinger et al. | |
| 5,164,170 A | * | 11/1992 | Rubin | 423/709 |
| 5,310,534 A | * | 5/1994 | Fajula et al. | 423/715 |
| 5,558,851 A | * | 9/1996 | Miller | 423/702 |
| 5,980,859 A | * | 11/1999 | Gajda et al. | 423/713 |
| 6,294,150 B2 | * | 9/2001 | Takahashi et al. | 423/716 |

FOREIGN PATENT DOCUMENTS

JP 11156198 A * 6/1999

* cited by examiner

*Primary Examiner*—David Sample
(74) *Attorney, Agent, or Firm*—Richard J. Sheridan (57) ABSTRACT

The present invention relates to new crystalline, molecular sieve CIT-6 that has the topology of zeolite beta. CIT-6 can be in an all-silica form, in a form wherein zinc is in the crystal framework, or a form containing silicon oxide and non-silicon oxides. In a preferred embodiment, CIT-6 has a crystal size of less than one micron and a water adsorption capacity of less than 0.05 g/g.

7 Claims, 1 Drawing Sheet

MOLECULAR SIEVE CIT-6

This application is a division of application no. 09/626,650, filed Jul. 27, 2000, now U.S. Pat. No. 6,521,206 B1 which is a division of application no. 09/288,247, filed Apr. 8, 1999, now U.S. Pat. No. 6,117,411 which is a continuation-in-part of application No. 09/106,598, filed Jun. 29, 1998, now abandoned.

BACKGROUND OF THE INVENTION

1. Field of the Invention

The present invention relates to new crystalline molecular sieve CIT-6, a method for preparing CIT-6 using a tetraethylammonium cation templating agent, a method of using CIT-6 as a precursor for making other crystalline molecular sieves, and processes employing CIT-6 as a catalyst.

2. State of the Art

Because of their unique sieving characteristics, as well as their catalytic properties, crystalline molecular sieves are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY OF THE INVENTION

The present invention is directed to a crystalline molecular sieve with unique properties, referred to herein as "molecular sieve CIT-6" or simply "CIT-6". When the CIT-6 contains a metal (or non-silicon) oxide, such as aluminum oxide, boron oxide, titanium oxide or iron oxide, it is referred to as "catalytically active" CIT-6.

The CIT-6 can be made in two forms. The first contains silicon oxide, zinc oxide and optional metal (or non-silicon) oxides (such as aluminum oxide), wherein the zinc is in the crystal framework of the CIT-6. This form of CIT-6 is referred to herein as "Zn-CIT-6".

Another form of CIT-6 is where the molecular sieve is composed only of silicon oxide. This form of CIT-6 is referred to herein as "all-Si CIT-6".

Zn-CIT-6 and all-Si CIT-6 each have the topology of zeolite beta.

In accordance with this invention, there is provided a molecular sieve comprising an oxide of silicon and an oxide of zinc and having the framework topology of zeolite beta, wherein the molecular sieve contains zinc in its crystal framework.

The present invention further provides such a molecular sieve having the topology of zeolite beta, and having a composition, as synthesized and in the anhydrous state, in terms of mole ratios as follows:

| | |
|---|---|
| $SiO_2/ZnO$ | 10–100 |
| $M/SiO_2$ | 0.01–0.1 |
| $Q/SiO_2$ | 0.07–0.14 | wherein M is lithium or a mixture of lithium and another alkali metal, and Q comprises a tetraethylammonium cation, wherein the molecular sieve contains zinc in its crystal framework.

Also in accordance with this invention there is provided a molecular sieve comprising silicon oxide, zinc oxide, and an oxide selected from aluminum oxide, boron oxide, gallium oxide, iron oxide, titanium oxide, vanadium oxide, zirconium oxide, tin-oxide or mixtures thereof and having the framework topology of zeolite beta, wherein the molecular sieve contains zinc in its crystal framework.

The present invention also provides such a molecular sieve having the topology of zeolite beta, and having a composition, as synthesized and in the anhydrous state, in terms of mole ratios as follows:

| | |
|---|---|
| $SiO_2/ZnO$ | 10–100 |
| $SiO_2/W$ | 30–250 |
| $M/SiO_2$ | 0.01–0.1 |
| $Q/SiO_2$ | 0.07–0.14 | wherein W is an oxide of aluminum, boron, gallium, vanadium, iron, titanium or mixtures thereof M is lithium or a mixture of lithium and another alkali metal and Q comprises a tetraethylammonium cation, wherein the molecular sieve contains zinc in its crystal framework.

Also provided in accordance with the present invention is a method of preparing a crystalline material comprising an oxide of silicon and an oxide of zinc and having the framework topology of zeolite beta, wherein the molecular sieve contains zinc in its crystal framework, said method comprising contacting in admixture under crystallization conditions sources of said oxides, a source of lithium or a mixture of lithium and another alkali metal and a templating agent comprising a tetraethylammonium cation.

The present invention also provides a method of preparing a crystalline material comprising an oxide of silicon, an oxide of zinc and an oxide selected from aluminum oxide, boron oxide, gallium oxide, vanadium oxide, iron oxide, titanium oxide or mixtures thereof and having the framework topology of zeolite beta, wherein the molecular sieve contains zinc in its crystal framework, said method comprising contacting in admixture under crystallization conditions sources of said oxides, a source of lithium or a mixture of lithium and another alkali metal and a templating agent comprising a tetraethylammonium cation.

Further provided by the present invention is a method of removing a tetraethylammonium organic template from the pores of a molecular sieve, said method comprising contacting the molecular sieve with acetic acid, or a mixture of acetic acid and pyridine at elevated temperature for a time sufficient to remove essentially all of the tetraethylammonium organic template from the molecular sieve. In a preferred embodiment, the molecular sieve has the topology of zeolite beta.

The present invention further provides a method of removing an organic template from the pores of a molecular sieve and at the same time removing zinc atoms from the framework of the molecular sieve, wherein the molecular sieve comprises an oxide of silicon, an oxide of zinc and, optionally an oxide selected from aluminum oxide, boron oxide, gallium oxide, vanadium oxide, iron oxide, titanium oxide or mixtures thereof and has the framework topology of zeolite beta, said method comprising contacting the molecular sieve with acetic acid or a mixture of acetic acid and pyridin at elevated temperature for a time sufficient to remove essentially all of the organic template and zinc from the molecular sieve. The present invention also provides the product of this method.

Also provided by the present invention is a method of making a crystalline material comprising (1) contacting in admixture under crystallization conditions a source of silicon oxide, a source of zinc oxide, a source of lithium or a mixture of lithium and another alkali metal and a templating agent comprising a tetraethylammonium cation until a crystalline material comprised of oxides of silicon and zinc and having the topology of zeolite beta is formed, (2) contacting the crystals with acetic acid or a mixture of acetic acid and pyridine at an elevated temperature of about 60° C. or less for a time sufficient to remove essentially all of the organic template and zinc from the crystals, and (3) contacting the crystals with a solution containing a source of aluminum, boron, gallium, iron, vanadium, titanium, zirconium, tin or mixtures thereof. The present invention also provides the product of this method.

This invention also provides a crystalline molecular sieve having the topology of zeolite beta, a crystal size of less than one micron and a water adsorption capacity of less than 0.05 g/g of molecular sieve.

Further provided by the present invention is a crystalline silicate molecular sieve having the topology of zeolite beta, a crystal size of less than one micron and a water adsorption capacity of less than 0.05 g/g of molecular sieve.

In addition, the present invention provides a method of preparing a crystalline material having the topology of zeolite beta comprising impregnating a silica-containing mesoporous material with an aqueous solution comprising tetraethylammonium cation in an amount sufficient to form a crystalline product having the topology of zeolite beta, and wherein the water to mesoporous material molar ratio is from about 0.5 to about 2, and subjecting the impregnated mesoporous material to crystallizing conditions of heat and pressure for a time sufficient to form crystals of a material having the topology of zeolite beta.

The present invention additionally provides a process for converting hydrocarbons comprising contacting a hydrocarbonaceous feed at hydrocarbon converting conditions with a catalyst comprising a catalytically active molecular sieve comprising silicon oxide, zinc oxide, and an oxide selected from aluminum oxide, boron oxide, gallium oxide, iron oxide, zirconium oxide, tin oxide or mixture thereof and having the framework topology of zeolite beta, wherein the molecular sieve contains zinc in its crystal framework. The molecular sieve may be predominantly in the hydrogen form, partially acidic or substantially free of acidity, depending on the process.

Further provided by the present invention is a hydrocracking process comprising contacting a hydrocarbon feedstock under hydrocracking conditions with a catalyst comprising the catalytically active molecular sieve of this invention, preferably predominantly in the hydrogen form.

This invention also includes a dewaxing process comprising contacting a hydrocarbon feedstock under dewaxing conditions with a catalyst comprising the catalytically active molecular sieve of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the catalytically active molecular sieve of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising at least one Group VIII metal and the catalytically active molecular sieve of this invention. The molecular sieve may be predominantly in the hydrogen form.

In accordance with this invention, there is also provided a process for catalytically dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15–3000 psi with a catalyst comprising at least one Group VIII metal and the catalytically active molecular sieve of this invention, preferably predominantly in the hydrogen form. The catalyst may be a layered catalyst comprising a first layer comprising at least one Group VIII metal and the catalytically active molecular sieve of this invention, and a second layer comprising an aluminosilicate zeolite which is more shape selective than the catalytically active molecular sieve of said first layer.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. and at a pressure of from about 15 psig to about 3000 psig in the presence of added hydrogen gas with a catalyst comprising at least one Group VIII metal and the catalytically active molecular sieve of this invention. The molecular sieve may be predominantly in the hydrogen form.

Further included in this invention is a process for isomerization dewaxing a raffinate comprising contacting said raffinate in the presence of added hydrogen with a catalyst comprising at least one Group VIII metal and the catalytically active molecular sieve of this invention. The raffinate may be bright stock, and the molecular sieve may be predominantly in the hydrogen form.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the catalytically active molecular sieve of this invention made substantially free of acidity by neutralizing said molecular sieve with a basic metal. Also provided in this invention is such a process wherein the molecular sieve contains a Group VIII metal component.

Also provided by the present invention is a catalytic cracking process comprising contacting a hydrocarbon feedstock in a reaction zone under catalytic cracking conditions in the absence of added hydrogen with a catalyst comprising the catalytically active molecular sieve of this invention, preferably predominantly in the hydrogen form. Also included in this invention is such a catalytic cracking process wherein the catalyst additionally comprises a large pore crystalline cracking component.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the catalytically active molecular sieve of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the catalytically active molecular sieve of this invention, preferably predominantly in the hydrogen form. The aromatic hydrocarbon and the polyalkyl aromatic hydrocarbon may be present in a molar ratio of from about 1:1 to about 25:1, respectively. The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the catalytically active molecular sieve of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the catalytically active molecular sieve of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the catalytically active molecular sieve of this invention.

The present invention further provides a process for oligomerizing olefins comprising contacting an olefin feed under oligomerization conditions with a catalyst comprising the catalytically active molecular sieve of this invention.

This invention also provides a process for converting lower alcohols and other oxygenated hydrocarbons comprising contacting said lower alcohol or other oxygenated hydrocarbon with a catalyst comprising the catalytically active molecular sieve of this invention under conditions to produce liquid products.

Also provided by the present invention is an improved process for the reduction of oxides of nitrogen contained in a gas stream in the presence of oxygen wherein said process comprises contacting the gas with a molecular sieve, the improvement comprising using as the molecular sieve, the molecular sieve of this invention. The molecular sieve may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

Further provided by the present invention is a method of removing liquid organic compounds from a mixture of liquid organic compounds and water, comprising contacting the mixture with an all-silica molecular sieve having the framework topology of zeolite beta, a crystal size less than one micron and a water adsorption capacity of less than 0.05 g/g of molecular sieve.

The present invention further provides a method of removing liquid organic compounds from a mixture of liquid organic compounds and water, comprising contacting the mixture with a molecular sieve comprising an oxide of silicon, an oxide of zinc and, optionally, an oxide selected from aluminum oxide, boron oxide, gallium oxide, iron oxide, vanadium oxide, titanium oxide, zirconium oxide, tin oxide and mixtures thereof, and having the framework topology of zeolite beta, wherein the molecular sieve contains zinc in its crystal framework.

DETAILED DESCRIPTION OF THE INVENTION

In preparing CIT-6 molecular sieves, a tetraethylammonium cation ("TEA") is used as a crystallization template (-also known as a structure directing agent, or SDA). The anion associated with the cation may be any anion which is not detrimental to the formation of the molecular sieve. Representative anions include halogen, e.g., fluoride, chloride, bromide and iodide, hydroxide, acetate, sulfate, tetrafluoroborate, carboxylate, and the like. Hydroxide is the most preferred anion.

In general, Zn-CIT-6 is prepared by contacting an active source of silicon oxide, an active source of zinc oxide, an active source of lithium or mixture of lithium and another alkali metal with the TEA templating agent.

Zn-CIT-6 is prepared from a reaction mixture having the following composition:

bM:cTEA:aZnO:SiO2:dH2O where M is lithium or a mixture of lithium and another alkali metal b=0.05–0.1; c=0.55–0.7; a=0.03–0.05; d=30–40. It is believed the concentrations of $Li^+$, $Zn^{2+}$ and TEAOH are critical to the formation of Zn-CIT-6.

When it is desired to prepare Zn-CIT-6 containing zinc oxide in combination with another metal oxide, such as aluminum oxide, a reaction mixture having the following composition:

bM:cTEA:aZnO:SiO2:e:dH2O where M is lithium or a mixture of lithium and another alkali metal, W is an oxide of aluminum, boron, gallium, vanadium, iron, titanium or mixtures thereof; b, c, a and d are as defined above and e=0.005–0.1.

In practice, Zn-CIT-6 is prepared by a process comprising:

(a) preparing an aqueous solution containing sources of silicon oxide, zinc oxide, lithium or a mixture of lithium and another alkali metal, TEA having an anionic counterion which is not detrimental to the formation of Zn-CIT-6, and, optionally, an oxide selected from aluminum oxide, boron oxide, gallium oxide, vanadium oxide, iron oxide, titanium oxide or mixtures thereof;

(b) maintaining the aqueous solution under conditions sufficient to form crystals of Zn-CIT-6; and (c) recovering the crystals of Zn-CIT-6.

The aqueous solution prepared in step (a) should be a clear solution. In some cases, heating a reaction mixture that is a white, cloudy mixture at room temperature will convert the mixture to a clear solution from which Zn-CIT-6 will form.

It has been discovered that higher amounts of TEA and lower reaction temperatures favor the formation of Zn-CIT-6.

Typical sources of silicon oxide include silicates, silica hydrogel, silicic acid, fumed silica, colloidal silica, tetra-alkyl orthosilicates, and silica hydroxides. Typical sources of zinc oxide include water-soluble zinc salts, such as zinc acetate. Typical sources of aluminum oxide for the reaction mixture include aluminates, alumina, aluminum colloids, aluminum oxide coated on silica sol, and hydrated alumina gels such as $Al(OH)_3$. Sources of boron, gallium, vanadium, iron and titanium compounds analogous to those listed for silicon and aluminum, and are known in the art.

Lithium or a mixture of lithium and another alkali metal is added to the reaction mixture. A variety of sources can be used, such as alkali metal hydroxides and alkali metal carbonates, with lithium hydroxide being particularly preferred. The lithium cation may be part of the as-synthesized crystalline oxide material, in order to balance valence electron charges therein. Other alkali metals which can be used in combination with the lithium include sodium and potassium, with the hydroxides being preferred, provided that lithium is the predominant alkali metal in the combination. The alkali metal (i.e., lithium or mixture of lithium and another alkali metal) may be employed in an amount of from about 0.05 to about 0.1 mole of alkali metal per mole of silica.

The reaction mixture is maintained at an elevated temperature until the crystals of the Zn-CIT-6 molecular sieve are formed. The hydrothermal crystallization is usually conducted under autogenous pressure, at about 100° C. to less than about 150° C. It has been discovered that higher reaction temperatures, e.g., 150° C. and higher, favor the formation of a molecular sieve having the topology of zeolite VPI-8 rather than the desired molecular sieve with the topology of zeolite beta. Preferably, the reaction temperature should be about 135° C. to 150° C.

The crystallization period is typically greater than 1 day to less than 7 days. The Zn-CIT-6 crystals should be recovered from the reaction mixture as soon as they form, since it has been discovered that under some circumstances if they remain in the reaction mixture for too long after formation, they can convert to a molecular sieve having the topology of VPI-8.

During the hydrothermal crystallization step, the Zn-CIT-6 crystals an be allowed to nucleate spontaneously from the reaction mixture. The use of Zn-CIT-6 crystals as seed material can be advantageous in decreasing the time necessary for complete crystallization to occur. In addition, seeding can lead to an increased purity of the product obtained by promoting the nucleation and/or formation of Zn-CIT-6 over any undesired phases. When used as seeds, Zn-CIT-6 crystals are added in an amount between 0.1 and 10% of the weight of silica used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized Zn-CIT-6 molecular sieve crystals. The drying step can be performed at atmospheric pressure or under vacuum.

Zn-CIT-6 has a composition, as synthesized and in the anhydrous state, in terms of mole ratios, shown in Table B below.

TABLE B

| As-Synthesized Zn-CIT-6 | |
| --- | --- |
| $SiO_2/ZnO$ | 10–100 |
| $M/SiO_2$ | 0.01–0.1 |
| $Q/SiO_2$ | 0.07–0.14 | where M and Q are as defined above.

Zn-CIT-6 can also have a composition, as synthesized and in the anhydrous state, in terms of mole ratios, shown in Table C below.

TABLE C

| As-Synthesized Zn-CIT-6 | |
| --- | --- |
| $SiO_2/ZnO$ | 10–100 |
| $SiO_2/W$ | 30–250 |
| $M/SiO_2$ | 0.01–0.1 |
| $Q/SiO_2$ | 0.07–0.14 | where W, M and Q are as defined above.

Solid state $^{29}Si$ NMR analysis and acidity measurements have shown that at least part of the zinc is in the framework of the Zn-CIT-6 crystals. Indeed, in one embodiment, the Zn-CIT-6 crystal framework contains only silicon, zinc and oxygen atoms, i.e., there are no other metals in this form of Zn-CIT-6.

Once the Zn-CIT-6 crystals have been formed and recovered, the organic template should be removed. This is typically done by calcining the crystals at high temperature until the organic template is removed. However, it has been discovered that calcination can be avoided by extracting the organic template from the molecular sieve. This extraction technique has advantages over calcination. For example, no calcination equipment is needed. Also, the organic template is not destroyed by the extraction, so it may be possible to recycle it, thereby reducing the cost of making the molecular sieve.

The organic template can be removed by contacting the Zn-CIT-6 crystals with acetic acid or a mixture of acetic acid and pyridine at a temperature of about 80° C. to about 135° C. for a period sufficient to remove essentially all of the organic template from the crystals (typically about two days). At the same time, the zinc is removed from the crystals, and they convert to all-Si CIT-6, i.e., an all-silica crystal having the framework topology of zeolite beta. As shown by water adsorption isotherms, all-Si CIT-6 is highly hydrophobic. $^{29}Si$ NMR analysis further shows that the crystal lattice has virtually no defects.

It has quite surprisingly been found that CIT-6 prepared as described above, i.e., the CIT-6 is prepared and then contacted with acetic acid or a mixture of acetic acid and pyridine at a temperature of about 80° C. to about 135° C. (referred to herein as "extraction"), is highly hydrophobic. This is in marked contrast to CIT-6 or beta zeolite in which the organic template has been removed by calcination.

Figure 1:
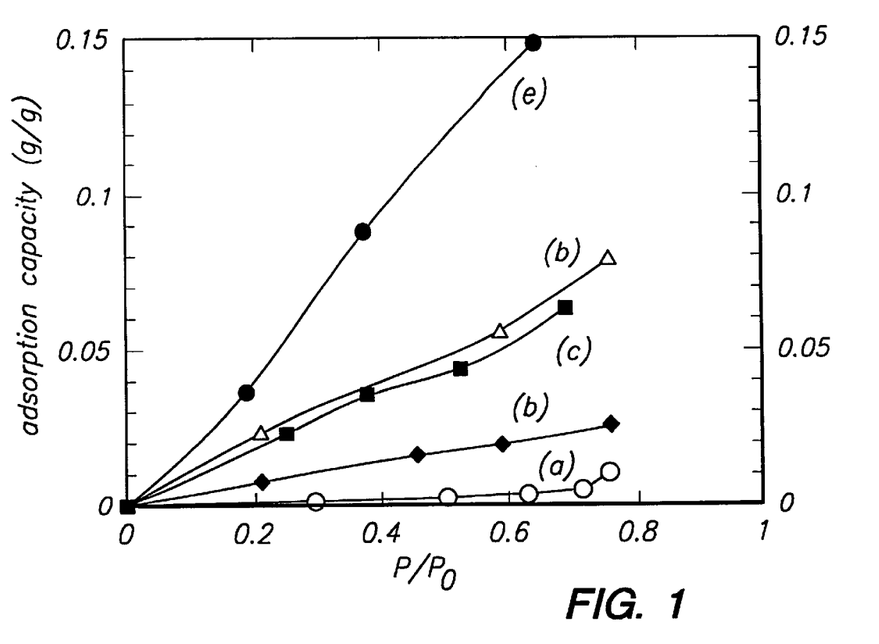
FIGS. 1 and 2 show the results of water adsorption isotherms at 25° C. of the molecular sieves of this invention and beta zeolite.

This phenomenon is illustrated in the FIG. 1. Five water adsorption isotherms are shown for the following materials:

(a) All-Si-CIT-6 prepared by extraction at 135° C.

(b) Zn-CIT-6 prepared using calcination (c) Silicoalumino-CIT-6 extracted at 60° C. followed by insertion of aluminum (d) Silicoalumino-CIT-6 prepared using aluminum oxide in the reaction mixture with the product extracted at 135° C.

(e) Calcined all-silica beta zeolite

The data indicate that the extracted aluminum-containing CIT-6 (sample d) is more hydrophobic than the sample prepared via aluminum insertion (sample c) and far more hydrophobic than the calcined zeolite beta (sample e). Calcined Zn-CIT-6 (sample b) likewise is far more hydrophobic than calcined zeolite beta, with extracted all-Si-CIT-6 (sample a) exhibiting the highest degree of hydrophobicity.

Alternatively, the extraction or removal of the organic template from Zn-CIT-6 can be accomplished by contacting the Zn-CIT-6 crystal with acetic acid or a mixture of acetic acid and pyridine at an elevated temperature of about 60° C. or less for a period sufficient to remove essentially all of the organic template from the crystals.

It has also been found that this latter extraction technique also removes some or all of the zinc atoms from the crystal framework. However, in this case the resultant molecular sieve contains internal silanol groups and other metals (or non-silicon atoms), such as aluminum, boron, gallium, vanadium, iron, titanium, zirconium, tin or mixtures thereof can be inserted into the crystal framework, replacing the zinc.

The metal can be inserted into the crystal framework by contacting the molecular sieve with a solution containing a source, such as a salt, of the desired metal. Although a wide variety of sources can be employed, chlorides and other halides, acetates, nitrates, and sulfates are particularly preferred. The preferred metals (or non-silicon atoms) are aluminum, boron, gallium, iron, titanium, vanadium, zirconium, tin, zinc and mixtures thereof. Representative techniques for inserting the metal are disclosed in a wide variety of patents including U.S. Pat. No. 3,140,249, issued Jul. 7, 1964 to Plank et al.; U.S. Pat. No. 3,140,251, issued on Jul. 7, 1964 to Plank et al.; and U.S. Pat. No. 3,140,253, issued on Jul. 7, 1964 to Plank et al., each of which is incorporated by reference herein. By way of example, aluminum can be inserted into the molecular sieve in place of some or all of the zinc by extracting the zinc (at about 60° C.) as described above, and then contacting the molecular sieve with an aluminum nitrate solution in about a 1:2:50 weight ratio of sieve:aluminum nitrate:water at about 80° C. for about one day.

As an alternative to making Zn-CIT-6, extracting the zinc and inserting, e.g., aluminum, an aluminosilicate can be made directly by synthesizing aluminozincosilicate CIT-6 as described above and in Example 27, and then extracting the zinc at the higher extraction temperature (135° C.). This removes the zinc from the CIT-6 and leaves an aluminosilicate molecular sieve with the topology of zeolite beta $^{27}$Al NMR analysis of aluminosilicates made in this manner shows that the aluminum remains in the crystal framework.

All-Si CIT-6 can be made by preparing Zn-CIT-6 as described above, followed by extraction of the zinc. It has surprisingly been found that all-Si CIT-6 made by this method has a much lower water adsorption capacity than all-silica zeolite beta made by traditional methods. The all-Si CIT-6 made by this method also has a crystal size of less than about one micron, whereas all-silica zeolite beta made by traditional method has a crystal size of greater than one micron, e.g., on the order of five microns. Furthermore, the all-Si CIT-6 made by this method has essentially no defect (i.e., Si—OH instead of Si—O—Si) sites, whereas all-silica zeolite beta made by traditional methods does contain defect sites that adsorb water.

A series of silica-containing mesoporous materials denoted M41S have been reported. These materials have been further classified, e.g., MCM-41 (hexagonal), MCM-48 (cubic) and others. These materials have uniform pores of 1.5–10 nm diameters, and are made by using a variety of surfactants as structure-directing agents. Non-silicon atom, e.g., Al, B, Ga, Ti, V, Zr, Fe, Mn, Sn, Zn, Cu and Nb, containing mesoporous materials have also been prepared.

The inorganic portion of MCM-41 resembles amorphous silicas rather than crystalline molecular sieves in terms of the local structure and bonding, but has many peculiar properties. It possesses uniformly sized mesopores with thin walls (around 10 Angstroms) and shows hydrophobic adsorption behavior.

It has now been discovered that zeolites having the topology of zeolite beta, in either all-silica form or in a form containing silica and metal (or non-silicon) oxide(s), can be made using the inorganic portion of ordered, mesoporous materials as reagents. The mesoporous materials may be all-silica, or they may contain silica and metal (or non-silicon) oxide(s), e.g., aluminum oxide. Examples of such mesoporous materials include, but are not limited to, MCM-41 and MCM-48.

The mesoporous materials are used in combination with tetraethylammonium cation organic templating agent, e.g., tetraethylammonium hydroxide (TEAOH). It has been found that, in order to assure the zeolite beta has essentially no defect sites, the reaction mixture containing the mesoporous material and TEAOH should be in the form of a "dry gel". The dry gel is made by impregnating the mesoporous material with an aqueous solution of TEAOH, allowing the resulting impregnated material to dry for about one day at room temperature. The thus-impregnated product should have a molar ratio of water to mesoporous material of about 0.5 to about 2, and contain sufficient TEAOH to cause formation of the beta structure. The impregnated material is then subject to crystallization conditions in an autoclave. The resulting crystalline product can either be calcined to remove the TEAOH, or it can be subjected to the extraction technique described above, thus assuring the product will be essentially defect-free.

If it is desired that the final product contain silicon oxide and a metal (or non-silicon) oxide, the mesoporous starting material can contain silicon oxide and the desired metal (or non-silicon) oxide. Metal oxides such as aluminum oxide, titanium oxide, vanadium oxide, zinc oxide, zirconium oxide, and magnesium oxide, as well as non-silicon oxides such as boron oxide, can be incorporated into the zeolite beta structure in this manner.

Figure 2:
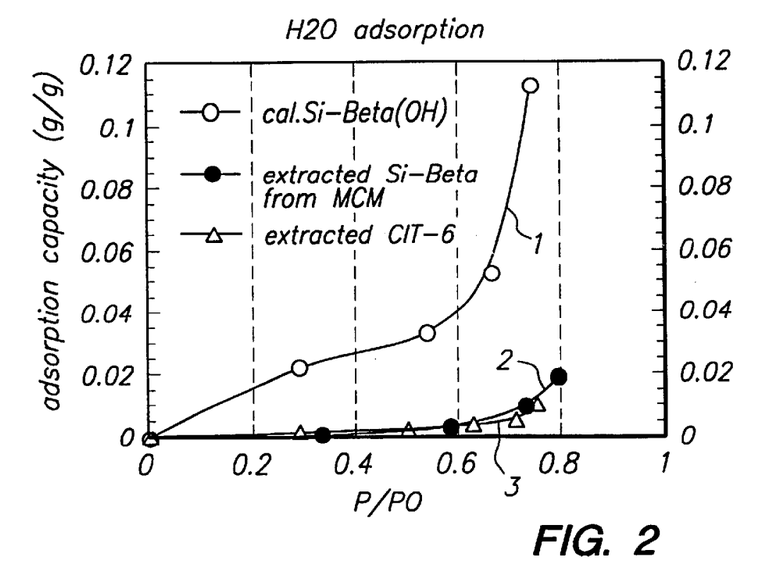

The molecular sieves made by either of these two techniques are highly hydrophobic. FIG. 2 shows the results of water adsorption isotherms for calcined all-silica beta zeolite (line 1), all-Si CIT-6 made from MCM-41 and subjected to extraction rather than calcination (line 2), and Zn-CIT-6 made by extraction (line 3). As can be seen, the water adsorption capacities of both the all-Si CIT-6 and Zn-CIT-6 are substantially lower than that of calcined all-silica beta zeolite.

When used in a catalyst, the molecular sieve can be used in intimate combination with hydrogenating components, such as tungsten, vanadium, molybdenum, rhenium, nickel, cobalt, chromium, manganese, or a noble metal such as palladium or platinum, for those applications in which a hydrogenation-dehydrogenation function is desired.

Metals may also be introduced into the molecular sieve by replacing some of the cations in the molecular sieve with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the catalytically active CIT-6. The molecular sieve can also be impregnated with the metals, or, the metals can be physically and intimately admixed with the molecular sieve using standard methods known to the art.

Typical ion-exchange techniques involve contacting the synthetic molecular sieve with a solution containing a salt of the desired replacing cation or cations. Although a wide variety of salts can be employed, chlorides and other halides, acetates, nitrates, and sulfates are particularly preferred. The molecular sieve is usually calcined prior to the ion-exchange procedure to remove the organic matter present in the channels and on the surface, since this results in a more effective ion exchange. Representative ion exchange techniques are disclosed in a wide variety of patents including U.S. Pat. No. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the molecular sieve is typically washed with water and dried at temperatures ranging from 65° C. to about 200° C. After washing, the molecular sieve can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of CIT-6, the spatial arrangement of the atoms which form the basic crystal lattice of the molecular sieve remains essentially unchanged.

Catalytically active CIT-6 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying, or, dried or partially dried and then extruded.

Catalytically active CIT-6 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

The catalytically active CIT-6 molecular sieves are useful in hydrocarbon conversion reactions. Hydrocarbon conversion reactions are chemical and catalytic processes in which carbon containing compounds are changed to different carbon containing compounds. Examples of hydrocarbon conversion reactions in which catalytically active CIT-6 is expected to be useful include hydrocracking, dewaxing, catalytic cracking and olefin and aromatics formation reactions. The catalysts are also expected to be useful in other petroleum refining and hydrocarbon conversion reactions such as polymerizing and oligomerizing olefinic or acetylenic compounds such as isobutylene and butene-1, reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives. The catalytically active CIT-6 catalysts may have high selectivity, and under hydrocarbon conversion conditions can provide a high percentage of desired products relative to total products.

The catalytically active CIT-6 molecular sieves can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

Depending upon the type of reaction which is catalyzed, the molecular sieve may be predominantly in the hydrogen form, partially acidic or substantially free of acidity. As used herein, "predominantly in the hydrogen form" means that, after calcination, at least 80% of the cation sites are occupied by hydrogen ions and/or rare earth ions.

The following table indicates typical reaction conditions which may be employed when using catalysts comprising catalytically active CIT-6 in the hydrocarbon conversion reactions of this invention. Preferred conditions are indicated in parentheses.

| Process | Temp., ° C. | Pressure | LHSV |
|---|---|---|---|
| Hydrocracking | 175–485 | 0.5–350 bar | 0.1–30 |
| Dewaxing | 200–475 (250–450) | 15–3000 psig (200–3000) | 0.1–20 (0.2–10) |
| Aromatics formation | 400–600 (480–550) | atm.–10 bar | 0.1–15 |
| Cat. cracking | 127–885 | subatm.–$^1$ (atm.–5 atm.) | 0.5–50 |
| Oligomerization | 232–649$^2$ 10–232$^4$ (27–204)$^4$ | 0.1–50 atm.$^{2,3}$ — — | 0.2–50$^2$ 0.05–20$^5$ (0.1–10)$^5$ |

-continued

| Process | Temp., °C. | Pressure | LHSV |
|---|---|---|---|
| Paraffins to aromatics | 100–700 | 0–1000 psig | 0.5–40[5] |
| Condensation of alcohols | 260–538 | 0.5–1000 psig | 0.5–50[5] |
| Xylene isomerization | 260–593[2] (315–566)[2] 38–371[4] | 0.5–50 atm.[2] (1–5 atm)[2] 1–200 atm.[4] | 0.1–100[5] (0.5–50)[5] 0.5–50 |

[1]Several hundred atmospheres
[2]Gas phase reaction
[3]Hydrocarbon partial pressure
[4]Liquid phase reaction
[5]WHSV Other reaction conditions and parameters are provided below.

Hydrocracking

Using a catalyst which comprises catalytically active CIT-6, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. No. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

Catalytically active CIT-6, preferably predominantly in the hydrogen form, can be used to dewax hydrocarbonaceous feeds by selectively removing straight chain paraffin. Typically, the viscosity index of the dewaxed product is improved (compared to the waxy feed) when the waxy feed is contacted with catalytically active CIT-6 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling above about 350° F.

A typical dewaxing process is the catalytic dewaxing of a hydrocarbon oil feedstock boiling above about 350° F. and containing straight chain and slightly branched chain hydrocarbons by contacting the hydrocarbon oil feedstock in the presence of added hydrogen gas at a hydrogen pressure of about 15–3000 psi with a catalyst comprising catalytically active CIT-6 and at least one Group VIII metal.

The catalytically active CIT-6 hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isodewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

Catalytically active CIT-6 may also be utilized as a dewaxing catalyst in the form of a layered catalyst. That is, the catalyst comprises a first layer comprising catalytically active molecular sieve CIT-6 and at least one Group VIII metal, and a second layer comprising an aluminosilicate zeolite which is more shape selective than catalytically active molecular sieve CIT-6. The use of layered catalysts is disclosed in U.S. Pat. No. 5,149,421, issued Sep. 22, 1992 to Miller, which is incorporated by reference herein in its entirety. The layering may also include a bed of catalytically active CIT-6 layered with a non-zeolitic component designed for either hydrocracking or hydrofinishing.

Catalytically active CIT-6 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig at space velocities (LHSV) between about 0.1 and 20 and a hydrogen recycle rate of about 400 to 1500 SCF/bbl. The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using catalytically active CIT-6. For example, a $C_{20+}$ lube oil may be made by isomerizing a $C_{20+}$ olefin feed over a catalyst comprising catalytically active CIT-6 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. and at a pressure of from about 15 psig to about 3000 psig in the presence of added hydrogen gas with a catalyst comprising catalytically active CIT-6 in the hydrogen form and at least one Group VIII metal.

Aromatics Formation

Catalytically active CIT-6 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising catalytically active CIT-6. It is also possible to convert heavier feeds into BTX or naphthalene derivatives of value using a catalyst comprising catalytically active CIT-6.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the molecular sieve with a basic metal, e.g., alkali metal, compound. Methods for rendering the catalyst free of acidity are known in the art. See the aforementioned U.S. Pat. No. 4,910,006 and U.S. Pat. No. 5,316,753 for a description of such methods.

The preferred alkali metals are sodium, potassium, rubidium and cesium.

Catalytic Cracking

Hydrocarbon cracking stocks can be catalytically cracked in the absence of hydrogen using catalytically active CIT-6, preferably predominantly in the hydrogen form.

When catalytically active CIT-6 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No. 5,316,753. When a traditional cracking catalyst (TC) component is employed, the relative weight ratio of the TC to the catalytically active CIT-6 is generally between about 1:10 and about 500:1, desirably between about 1:10 and about 200:1, preferably between about 1:2 and about 50:1, and most preferably is between about 1:1 and about 20:1. The novel molecular sieve and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Alkylation and Transalkylation

Catalytically active CIT-6 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising catalytically active CIT-6.

Catalytically active CIT-6 can also be used for removing benzene from gasoline by alkylating the benzene as described above and removing the alkylated product from the gasoline.

For high catalytic activity, the catalytically active CIT-6 molecular sieve should be predominantly in its hydrogen ion form. It is preferred that, after calcination, at least 80% of the cation sites are occupied by hydrogen ions and/or rare earth ions.

Examples of suitable aromatic hydrocarbon feedstocks which may be alkylated or transalkylated by the process of the invention include aromatic compounds such as benzene, toluene and xylene. The preferred aromatic hydrocarbon is benzene. There may be occasions where naphthalene derivatives may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F., preferably 250° F. to 450° F. The reaction pressure should be sufficient to maintain at least a partial liquid phase in order to retard catalyst fouling. This is typically 50 psig to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F., but it is preferably about 250° F. to 450° F. The reaction pressure should be sufficient to maintain at least a partial liquid phase, typically in the range of about 50 psig to 1000 psig, preferably 300 psig to 600 psig. The weight hourly space velocity will range from about 0.1 to 10. U.S. Pat. No. 5,082,990 issued on Jan. 21, 1992 to Hsieh, et al. describes such processes and is incorporated herein by reference.

Isomerization of Olefins

Catalytically active CIT-6 can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40–60 weight percent normal butenes. A methyl-tert-butyl ether unit effluent typically contains 40–100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the catalytically active CIT-6. The process may be carried out generally at a temperature from about 625° F. to about 950° F. (329–510° C.), for butenes, preferably from about 700° F. to about 900° F. (371–482° C.), and about 350° F. to about 650° F. (177–343° C.) for pentenes and hexenes. The pressure ranges from subatmospheric to about 200 psig, preferably from about 15 psig to about 200 psig, and more preferably from about 1 psig to about 150 psig.

The liquid hourly space velocity during contacting is generally from about 0.1 to about 50 $hr^{-1}$, based on the hydrocarbon feed, preferably from about 0.1 to about 20 $hr^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Conversion of Paraffins to Aromatics

Catalytically active CIT-6 can be used to convert light gas $C_2$-$C_6$ paraffins to higher molecular weight hydrocarbons including aromatic compounds. Preferably, the molecular sieve will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Xylene Isomerization

Catalytically active CIT-6 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics steam may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt. % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt. % of a diluent such as toluene, trimethylbenzene, naphthenes or paraffins.

Oligomerization

It is expected that catalytically active CIT-6 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising catalytically active CIT-6.

The molecular sieve can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the molecular sieve have a fairly low aromatization activity, i.e., in which the amount of aromatics produced is not more than about 20% by weight. This is accomplished by using a molecular sieve with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such molecular sieves may be obtained by steaming, by use in a conversion process or by any other method which may occur to one skilled in this art.

Condensation of Alcohols

Catalytically active CIT-6 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Other Uses for CIT-6

CIT-6 can also be used as an adsorbent with high selectivities based on molecular sieve behavior and also based upon preferential hydrocarbon packing within the pores.

CIT-6 is a hydrophobic material that can be used to remove some organic compounds from water.

CIT-6 may also be used for the catalytic reduction of the oxides of nitrogen in a gas stream. Typically, the gas stream also contains oxygen, often a stoichiometric excess thereof. Also, the CIT-6 may contain a metal or metal ions within or on it which are capable of catalyzing the reduction of the nitrogen oxides. Examples of such metals or metal ions include copper, cobalt and mixtures thereof.

One example of such a process for the catalytic reduction of oxides of nitrogen in the presence of a molecular sieve is disclosed in U.S. Pat. No. 4,297,328, issued Oct. 27, 1981 to Ritscher et al., which is incorporated by reference herein. There, the catalytic process is the combustion of carbon monoxide and hydrocarbons and the catalytic reduction of the oxides of nitrogen contained in a gas stream, such as the exhaust gas from an internal combustion engine. The molecular sieve used is metal ion-exchanged, doped or loaded sufficiently so as to provide an effective amount of catalytic copper metal or copper ions within or on the molecular sieve. In addition, the process is conducted in an excess of oxidant, e.g., oxygen.

Oxidation

Titanium-containing CIT-6 may be used as a catalyst in oxidation reactions.

The oxidizing agent employed in the oxidation processes of this invention is a hydrogen peroxide source such as hydrogen peroxide ($H_2O_2$) or a hydrogen peroxide precursor (i.e., a compound which under the oxidation reaction conditions is capable of generating or liberating hydrogen peroxide).

The amount of hydrogen peroxide relative to the amount of substrate is not critical, but must be sufficient to cause oxidation of at least some of the substrate. Typically, the molar ratio of hydrogen peroxide to substrate is from about 100:1 to about 1:100, preferably 10:1 to about 1:10. When the substrate is an olefin containing more than one carbon-carbon double bond, additional hydrogen peroxide may be required. Theoretically, one equivalent of hydrogen peroxide is required to oxidize one equivalent of a mono-unsaturated substrate, but it may be desirable to employ an excess of one reactant to optimize selectivity to the epoxide. In particular, the use of a moderate to large excess (e.g., 50 to 200%) of olefin relative to hydrogen peroxide may be advantageous for certain substrates.

If desired, a solvent may additionally be present during the oxidation reaction in order to dissolve the reactants other than the Ti-containing CIT-6, to provide better temperature control, or to favorably influence the oxidation rates and selectivities. The solvent, if present, may comprise from 1 to 99 weight percent of the total oxidation reaction mixture and is preferably selected such that it is a liquid at the oxidation reaction temperature. Organic compounds having boiling points at atmospheric pressure of from about 50° C. to about 150° C. are generally preferred for use. Excess hydrocarbon may serve as a solvent or diluent. Illustrative examples of other suitable solvents include, but are not limited to, ketones (e.g., acetone, methyl ethyl ketone, acetophenone), ethers (e.g., tetrahydrofuran, butyl ether), nitrites (e.g., acetonitrile), aliphatic and aromatic hydrocarbons, halogenated hydrocarbons, and alcohols (e.g., methanol, ethanol, isopropyl alcohol, t-butyl alcohol, alpha-methyl benzyl alcohol, cyclohexanol). More than one type of solvent may be utilized. Water may also be employed as a solvent or diluent.

The reaction temperature is not critical, but should be sufficient to accomplish substantial conversion of the substrate within a reasonably short period of time. It is generally advantageous to carry out the reaction to achieve as high a hydrogen peroxide conversion as possible, preferably at least about 50%, more preferably at least about 90%, most preferably at least about 95%, consistent with reasonable selectivities. The optimum reaction temperature will be influenced by catalyst activity, substrate reactivity, reactant concentrations, and type of solvent employed, among other factors, but typically will be in a range of from about 0° C. to about 150° C. (more preferably from about 25° C. to about 120° C.). Reaction or residence times from about one minute to about 48 hours (more desirably from about ten minutes to about eight hours) will typically be appropriate, depending upon the above-identified variables. Although subatmospheric pressures can be employed, the reaction is preferably performed at atmospheric or at elevated pressure (typically, between one and 100 atmospheres), especially when the boiling point of the substrate is below the oxidation reaction temperature. Generally, it is desirable to pressurize the reaction vessel sufficiently to maintain the reaction components as a liquid phase mixture. Most (over 50%) of the substrate should preferably be present in the liquid phase.

The oxidation process of this invention may be carried out in a batch, continuous, or semi-continuous manner using any appropriate type of reaction vessel or apparatus such as a fixed bed, transport bed, fluidized bed, stirred slurry, or CSTR reactor. The reactants may be combined all at once or sequentially. For example, the hydrogen peroxide or hydrogen peroxide precursor may be added incrementally to the reaction zone. The hydrogen peroxide could also be generated in situ within the same reactor zone where oxidation is taking place.

Once the oxidation has been carried out to the desired degree of conversion, the oxidized product may be separated and recovered from the reaction mixture using any appropriate technique such as fractional distillation, extractive distillation, liquid-liquid extraction, crystallization, or the like.

Additional details for oxidation reactions are disclosed in U.S. Pat. No. 5,869,706, issued Feb. 9, 1999 to Dartt and Davis, which is incorporated herein by reference in its entirety.

Vanadium-containing CIT-6 may be used as a catalyst in the oxidation/dehydrogenation of hydrocarbons. For example, vanadium-containing CIT-6 may be used to partially (or completely) oxidize hydrocarbons in the presence of oxygen (air) or hydrogen peroxide. The oxidation may either be complete, i.e., oxidizing the hydrocarbon to carbon dioxide, or partial, as in the oxidation of propane to propylene. The reaction is conducted under conditions that yield the desired degree of oxidation, and are known in the art.

EXAMPLES

The following examples demonstrate but do not limit the present invention.

Examples 1–25

Synthesis of Zn-CIT-6

Zn-CIT-6 reaction mixtures are prepared by the following method. After the organic and inorganic cations are dissolved in distilled water, zinc acetate dihydrate is added. Next, silica is added and the mixture is stirred for two hours.

The starting mixtures are each charged into Teflon-lined, stainless autoclaves and heated statically in convection ovens. The products are collected by vacuum filtration, washed with distilled water, and dried in air at room temperature. In order to remove the occluded organic molecules, the product is heated in air to 540° C. within six hours and maintained at this temperature for six hours. An as-made Zn-CIT-6 is treated with 1 M aqueous ammonium nitrate solution at 80° C. for ten hours. The treated sample is recovered by vacuum filtration and washed with distilled water. This procedure is repeated four times. The final material is dried in air at room temperature.

Using the above procedure, the products indicated below are made from a reaction mixture having the following composition:

bLiOH:cTEAOH:aZn(CH$_3$COO).2H$_2$O:SiO2:dH$_2$O

| Example No. | b | c | a | D | Temp. (° C.) | Days | Product |
|---|---|---|---|---|---|---|---|
| 1 | 0.05 | 0.55 | 0.03 | 30 | 150 | 3 | CIT-6 |
| 2 | 0.05 | 0.55 | 0.03 | 30 | 150 | 5 | CIT-6 + VPI-8 |
| 3 | 0.05 | 0.55 | 0.03 | 30 | 150 | 7 | VPI-8 |
| 4 | 0.2 | 0.4 | 0.03 | 30 | 150 | 3 | VPI-8 |
| 5 | 0.05 | 0.55 | 0.03 | 30 | 175 | 2 | Amorph. |
| 6 | 0.05 | 0.55 | 0.03 | 30 | 175 | 3 | VPI-8 |
| 7 | 0.05 | 0.55 | 0.03 | 30 | 135 | 9 | CIT-6 |
| 8 | 0.05 | 0.55 | 0.03 | 30 | 135 | 15 | CIT-6 |
| 9 | 0.05 | 0.55 | 0.03 | 30 | 135 | 18 | VPI-8 |
| 10 | 0.05 | 0.45 | 0.03 | 30 | 150 | 6 | VPI-8 |
| 11 | 0.05 | 0.55 | 0.03 | 30 | 150 | 4 | CIT-6 |
| 12 | 0.05 | 0.55 | 0.03 | 30 | 150 | 6 | VPI-8 |
| 13 | 0.05 | 0.6 | 0.03 | 30 | 150 | 4 | CIT-6 |
| 14 | 0.05 | 0.6 | 0.03 | 30 | 150 | 29 | VPI-8 + small amnt. CIT-6 |
| 15 | 0.05 | 0.65 | 0.03 | 30 | 150 | 4 | CIT-6 |
| 16 | 0.05 | 0.65 | 0.03 | 30 | 150 | 17 | CIT-6 + small amnt. VPI-8 |
| 17 | 0.05 | 0.65 | 0.03 | 40 | 150 | 4 | CIT-6 |
| 18 | 0.05[1] | 0.65 | 0.03 | 30 | 150 | 14 | Amorph. |
| 19 | 0.05 | 0.6 | 0.01 | 30 | 150 | 11 | Amorph. + small amnt. MFI |
| 20 | 0.05 | 0.6 | 0.01 | 30 | 150 | 18 | MFI |
| 21 | 0.05 | 0.55 | — | 30 | 150 | 5 | MTW |
| 22 | 0.05 | 0.65 | 0.05 | 30 | 150 | 4 | CIT-6 + small amnt. VPI-8 |
| 23 | 0.02 | 0.6 | 0.03 | 30 | 150 | 17 | Amorph. |
| 24 | 0.1 | 0.6 | 0.03 | 30 | 150 | 4 | Unknown + CIT-6 |
| 25[2,3] | 0.05 | 0.7 | 0.03 | 30 | 150 | 4 | CIT-6 |

[1]NaOH used instead of LiOH.
[2]Silica source is Cab-O-Sil M5 fumed silica. All others are HS-30.
[3]Milky white mixture heated at 80° C. for three hours to get a clear solution.

The results above demonstrate that (1) too long a reaction time can produce VPI-8 instead of Zn-CIT-6 (Ex. 3, 9, 12, 14 and 17); (2) too high a reaction temperature may not produce Zn-CIT-6 (Ex. 5 and 6); (3) the presence and concentration of lithium is critical to formation of Zn-CIT-6 (Ex. 4, 18 and 22); and the presence and concentration of zinc is critical to formation of Zn-CIT-6 (Ex. 19, 20 and 21).

Example 26

Synthesis of Zincoaluminosilicate CIT-6

A solution of tetraethylammonium hydroxide (4.10 grams of a 35 wt. % solution) is added to 3.34 grams of water. To this is added 0.018 gram of LiOH, 0.098 gram of zinc acetate dihydrate, and 0.056 gram of Al(NO$_3$)$_3$.9H$_2$O and the resulting mixture stirred. Three grams of Ludox HS-30 silica is added and the resulting mixture stirred for two hours. The resulting solution is charged into a Teflon-lined autoclave, and heated (statically) at 150° C. for four days. The product was CIT-6 containing both zinc and aluminum in the crystal framework.

Example 27

Extraction of TEA and Zinc

The TEA and zinc are extracted from the CIT-6 prepared in Example 26 by contacting 0.1 gram of the aluminozincosilicate CIT-6 with a solution containing 6 ml acetic acid, 1 ml pyridine and 10 ml water at 135° C. for two days. The TEA and zinc are extracted from the CIT-6, but the aluminum remains in the crystal framework, as shown by $^{27}$Al NMR.

Example 28

Cyclohexane Adsorption

The adsorption amount of vapor-phase cyclohexane (99.5%, EM) for Zn-CIT-6 is measured at 25° C. using a McBaine-Bakr balance. Prior to the adsorption experiment, calcined samples of CIT-6 are dehydrated at 350° C. under vacuum for five hours. The saturation pressure, $P_0$, of cyclohexane is 97.5 mm Hg. The adsorption is performed at a cyclohexane pressure of 30 mm Hg. The amount of adsorbed cyclohexane of the Zn-CIT-6 sample is 0.16 ml/g.

Example 29

Extraction of TEA and Zinc

The TEA and zinc are extracted from Zn-CIT-6 by contacting 0.1 gram of CIT-6 with a solution containing 6 ml acetic acid, 0.1 ml pyridine and 10 ml water at 60° C. for three days.

Example 30

Insertion of Aluminum

Aluminum is inserted into the product of Example 29 by contacting the product with an aqueous solution of aluminum nitrate at a 1:2:50 weight ratio of Zn-CIT-6:aluminum nitrate:water at 80° C. for one day.

Example 31

Insertion of Titanium

Titanium is inserted into the product of Example 29 by contacting the product with 1.5 ml 1M $TiCl_4$ toluene solution and 10 ml toluene at 80° C. for 12 hours under nitrogen atmosphere. After treatment, the sample is filtrated, washed with acetone and dried. UV analysis of the resultant product shows that titanium is inserted in the product.

Example 32

Preparation of Pd—Zn-CIT-6

2.84 grams of Zn-CIT-6 synthesized as in Example 1 is calcined to 540° C. in a mixture of air and nitrogen, and subsequently ion-exchanged once with ammonium nitrate at 85° C. for two hours, recovered and dried to 300° C. Pd acetylacetonate (0.0286 gms) in toluene (2.25 ml) is admitted into a sealed bottle in which the heated Zn-CIT-6 has been place. This provides for some vacuum at room temperature. The bottle is manually shaken while the solution is admitted by syringe. The wetted solid is allowed to stand overnight. Next the material is calcined to 425° C. in air.

Example 33

Catalytic Activity

The Pd—Zn-CIT-6 prepared in Example 30 is loaded as 24–40 mesh particles into a stainless steel reactor. 0.50 Gram is packed into a ⅜ inch stainless steel tube with alundum on both sides of the zeolite bed. A Lindburg furnace is used to heat the reactor tube. Helium is introduced into the reactor tube at 10 cc/min. and at atmospheric pressure. The reactor is heated to about 372° C., and a 50/50 (w/w) feed of n-hexane and 3-methylpentane is introduced into the reactor at a rate of 8 $\mu$l/min. Feed delivery is made via a Brownlee pump. Direct sampling into a gas chromatograph begins after 10 minutes of feed introduction. At 800° F. (427° C.) and 10 minutes on stream the catalyst gives 47% conversion with the products being about ⅓ aromatics, ⅓ isomerized $C_6$ and a third olefins from dehydrogenation. There is a few percent cracked product. There is no preference for reaction of either isomer.

Example 34

Synthesis of All-Si CIT-6 From All-silica Mesoporous Material

MCM-41 is prepared using the following gel composition where $C_{16}$TMA is hexadecyltrimethylammonoium:

$SiO_2/0.39Na_2O/0.26(C_{16}TMA)_2O/0.14H_2SO_4/0.51HBr/62.53H_2O$

The gel is placed in an autoclave at 120° C. for three days. The resulting MCM-41 crystals are recovered and calcined at 540° C. for ten hours.

The calcined MCM-41 (0.1 gram) is impregnated with 0.3 gram of 35 wt. % TEAOH aqueous solution and dried at room temperature for one day (TEAOH/Si=0.4, $H_2O$/Si= ~2). The resulting powder is charged into an autoclave and heated at 150° C. for seven days. The product is all-silica zeolite beta.

0.1 Gram of the all-silica zeolite beta (still containing TEAOH) is treated with a mixture of 6 ml acetic acid and 10 ml water at 135° C. for two days. Almost all of the TEAOH is removed from the material, and it retains the beta zeolite structure. The resulting product is highly hydrophobic.

Example 35

Synthesis of Si-MCM-41

Si-MCM-41 materials (Si-1-MCM-41) are prepared by adding 2.4 grams of 29 wt. % $NH_4OH$ solution (EM) to 26.4 grams of 29 wt % hexadecyltrimethylammonium chloride ($C_{16}$TMACl) solution. This solution is combined with 2.3 grams of tetramethylammonium hydroxide pentahydrate (TMAOH.5$H_2O$), 20 grams of tetramethylammonium silicate (10 wt. % $SiO_2$, TMA/Si=0.5) and 4.5 grams of fumed silica (Cab-O-Sil M-5 from Cabot) under stirring. The composition of the resulting gel is:

$SiO_2:0.11(C_{16}TMA)_2O:0.09(NH_4)_2O:0.11HCl:19.3H_2O.$

The reaction mixture is charged into a Teflon-lined, stainless steel autoclave and heated statically at 140° C. for three days. The product is collected by vacuum filtration, washed with water and dried in air at room temperature. In order to remove occluded molecules, the as-made sample is calcined in air at 550° C. within six hours and maintained at this temperature for six hours. The product is identified as MCM-41 and designated Si-1-MCM-41.

Example 36

Synthesis of Si-MCM-41

Concentrated $H_2SO_4$ (1.2 grams) is added dropwise to 20 grams of sodium silicate (10.8 wt. % $Na_2O$, 27.0 wt. % $SiO_2$ and 62.2 wt. % $H_2O$) in 42.8 grams of water under stirring. Next, 16.8 grams of $C_{16}$TMABr in 50.3 grams of water is added to the solution and the resulting mixture is stirred for two hours. The resulting gel has the composition:

$SiO_2:0.26(C_{16}TMA)_2O:0.39Na_2O:0.14H_2SO_4:0.51HBr:62.5H_2O.$

The reaction mixture is charged into a Teflon-lined, stainless steel autoclave and heated statically at 120° C. for three days. The product is collected by vacuum filtration, washed with water and dried in air at room temperature and calcined in air at 550° C. within six hours and maintained at this temperature for six hours to remove the organic molecules. The organic molecules occluded in the pores of the material are also removed by contacting the as-made sample with 1M HCl solution in diethyl ether at room temperature. The product is identified as MCM-41 and designated Si-2-MCM-41.

Example 37

Synthesis of MCM-48

NaOH (0.8 gram) is dissolved in 44 grams of water. To this solution is added 8.89 grams of $C_{16}$TMABr and finally 8.33 grams of TEOS is added to it. The resulting mixture is stirred at room temperature for two hours. The mixture has the following composition:

$$SiO_2:0.61C_{16}TMABr:60H_2O:0.5NaOH:4EtOH.$$

The reaction mixture is charged into a Teflon-lined, stainless steel autoclave and heated statically at 105° C. for three days. The product is collected by vacuum filtration, washed with water and dried in air at room temperature and calcined in air at 550° C. within six hours and maintained at this temperature for six hours to remove the organic molecules. The product is identified as MCM-48.

Example 38

Synthesis of Al-Containing MCM-41

2.4 Grams of 29 wt. % $NH_4OH$ solution is added to 26.4 grams of 29 wt. % $C_{16}$TMACl solution. To this, 0.37 gram of sodium aluminate (54 wt. % $Al_2O_3$, 41 wt. % $Na_2O$, 5 wt. % $H_2O$) is added and the solution is combined with 2.3 grams of TMAOH.5$H_2O$, 20 grams of tetramethylammonium silicate (10 wt. % $SiO_2$, TMA/Si=0.5) and 4.5 grams of fumed silica (Cab-O-Sil M-5) under stirring. The resulting gel composition is:

$$SiO_2:0.02\ Al_2O_3:0.02Na_2O:0.11(C_{16}TMA)_2O:0.13(TMA)_2O:0.09(NH_4)_2O:0.22\ HCl:19.3\ H_2O.$$

The reaction mixture is charged into a Teflon-lined, stainless steel autoclave and heated statically at 135° C. for three days. The product is collected by vacuum filtration, washed with water and dried in air at room temperature. In order to remove the occluded molecules, the as-made sample is calcined in air at 550° C. within six hours and maintained at this temperature for six hours. The product is identified as MCM-41 containing aluminum in its framework, and is designated Al-MCM-41.

Example 39

Synthesis of B-Containing MCM-41

A mixture of 1 gram of fumed silica (Cab-O-Sil M5) and 6.4 grams of water are mixed under vigorous stirring. After ten minutes of mixing, a solution of 3.3 grams of $C_{16}$TMABr in 21.7 grams of water is added to this slurry. After another ten minutes of stirring, a third solution containing 2.9 grams of tetramethylammonium silicate solution (10 wt. % $SiO_2$, TMA/Si=0.5) and 1.4 grams of sodium silicate is added to the slurry. $H_3BO_3$ (0.034 gram) is added and the mixing continued for 30 minutes. The resulting gel has the composition:

$$SiO_2:0.02H_3BO_3:0.16C_{16}TMABr:0.085Na_2O:63H_2O.$$

The reaction mixture is charged into a Teflon-lined, stainless steel autoclave and heated statically at 100° C. for one day. The product is collected by vacuum filtration, washed with water and dried in air at room temperature and calcined under nitrogen for temperatures up to 550° C. within six hours and maintained at this temperature for two hours before slowly switching from nitrogen to air. After an additional four hours at 500° C., the sample is cooled to room temperature. The product is identified as MCM-41 containing boron in its framework, and is designated B-MCM-41.

Example 40

Synthesis of V-Containing MCM-41

6.24 Grams of tetraethyl orthosilicate (TEOS), 0.16 gram of vanadyl acetylacetonate, 9 grams of ethanol, and 1.8 of isopropyl alcohol are mixed together (Solution A). A second solution (B) contains 1.5 grams of dodecylamine ($C_{12}A$), 0.6 gram of 1 N HCl and 19 grams of water. Solution A is added slowly to Solution B under vigorous stirring. The resulting reaction mixture has the following composition:

$$SiO_2:0.02VO(acac)_2:0.27C_{12}A:0.02HCl:36H_2O:10.5EtOH:1iPrOH.$$

The mixture is stirred at room temperature for 12 hours. The product is collected by vacuum filtration, washed with water and dried in air at room temperature and calcined in air at 550° C. within six hours and maintained at this temperature for six hours to remove organic molecules. The product is identified as MCM-41 containing vanadium in its framework, and is designated V-MCM-41.

Example 41

Synthesis of Zr-Containing MCM-41

Solution A is prepared by mixing 10.42 grams of TEOS, 0.47 gram of zirconium propoxide (70 wt. % solution in 1-propanol). A second solution (B) contains 4 grams of octadecylamine ($C_{18}A$), 15 grams of ethanol and 27 grams of water. Solution A is added slowly to Solution B under vigorous stirring. The resulting reaction mixture has the following composition:

$$SiO_2:0.02\ ZrO_2:0.3C_{18}A:30H_2O:10.5EtOH:2.5\ PrOH.$$

The mixture is stirred at room temperature for 12 hours. The product is collected by vacuum filtration, washed with water and dried in air at room temperature and calcined in air at 550° C. within six hours and maintained at this temperature for six hours to remove organic molecules. The product is identified as MCM-41 containing zirconium in its framework, and is designated Zr-MCM-41.

Example 42

Synthesis of Zn-Containing MCM-41

0.18 Gram of zinc acetate dihydrate ($Zn(OAc)_2.2H_2O$) and 0.8 gram of NaOH are dissolved in 44 grams of water. 8.89 Grams of $C_{16}$TMABr is added to this solution and finally 8.33 grams of TEOS is added. The resulting mixture is stirred at room temperature for two hours. The reaction mixture has the following composition:

$$SiO_2:0.02\ Zn(OAc)_2:0.61C_{16}TMABr:60H_2O:0.5NaOH:4EtOH$$

The reaction mixture was charged into a Teflon-line, stainless steel autoclave and heated statically at 105° C. for three days. The product is collected by vacuum filtration, washed with water and dried in air at room temperature and calcined in air at 550° C. within six hours and maintained at this temperature for six hours to remove organic molecules. The product is identified as MCM-41 containing zinc in its framework, and is designated Zn-MCM-41.

Examples 43–49

Synthesis of CIT-6 from Mesoporous Materials

Calcined, mesoporous materials are each in turn impregnated with 35 wt. % TEAOH aqueous solution and dried at room temperature for 12 hours. The resulting powder is charged into a Teflon-lined autoclave and heated at 150° C. statically. The product is washed with distilled water and dried in air at room temperature. In order to remove the occluded molecules, the as-made sample is calcined in air at 550° C. within six hours and maintained at this temperature for six hours. The organic molecules occluded in the pores of the as-made sample are also removed by contacting the as-made sample with acetic acid at 135° C. for two days.

A typical procedure is as follows: 0.1 gram of calcined Si-MCM-41 is impregnated with 0.3 gram of 35 wt. % TEAOH aqueous solution (TEAOH/Si=0.4) and dried at room temperature for 12 hours ($H_2O/SiO_2$ molar ratio is about 1.5). The resulting powder is heated at 150° C. for one week in an autoclave. The yield of crystalline solid after calcination is about 80%. Conditions for specific materials are shown in the table below.

| Example Number | Non-Si Atom Containing Mesoporous Material[a] | Impregnated TEAOH/Si Ratio | Conditions | Result[a] |
|---|---|---|---|---|
| 43 | Al-MCM-41 (26) | 0.4 | 150° C. × 7 days | Al-Beta (26) |
| 44 | B-MCM-41 (54) | 0.4 | 150° C. × 7 days | B-Beta (62) |
| 45 | Ti-MCM-41 (47) | 0.4 | 150° C. × 7 days | Ti-Beta (47) |
| 46 | Si-MCM-41 | 0.4 + Ti (0.02) | 150° C. × 7 days | Si-Beta (63) |
| 47 | V-MCM-41 (59) | 0.4 | 150° C. × 7 days | V-Beta (148) |
| 48 | Zr-MCM-41 (47) | 0.4 | 150° C. × 7 days | Zr-Beta (73) |
| 49 | Zn-MCM-41 (33) | 0.4 | 150° C. × 7 days | Zn-Beta (30) |

[a]Values in parentheses are the Si/Y molar ratios (Y = Al, B, Ti, V, Zr or Zn) in the as-made product, measured by elemental analysis.

The as-made materials are then calcined to remove the TEA cations.

Example 50

Synthesis of Ti-Containing CIT-6

Calcined Si-MCM-41 is impregnated with a solution containing titanium tetraisopropoxide (Ti/Si=0.02) and a 35 wt. % aqueous solution of TEAOH (TEA/Si=0.4). The impregnated solid is treated as described above in Examples 43–49. The resulting product is CIT-6 containing titanium in its framework.

The results above clearly indicate that a highly crystalline all-Si-CIT-6 is formed from Si-MCM-41 using TEAOH as the organic template (or structure directing agent). When $Na^+$ was added to the reaction mixture, it was found that all-Si-CIT-6 is formed faster than in the absence of $Na^+$. It was also found that when fumed silica was used as the silica source, only amorphous phases were obtained, even if $Na^+$ is added. Conventional hydrothermal reaction ($H_2O/Si=20$) yields only amorphous products as well. When using MCM-48 as a silica source, all-Si-CIT-6 is also formed. These data indicate that mesoporous silicas such as MCM-41 and MCM-48 can be used to synthesize all-Si-CIT-6, that $Na^+$ cations promote the conversion to all-Si-CIT-6 and that the mesoporous materials can also be used to prepare CIT-6.

What is claimed is:

1. A crystalline molecular sieve having the topology of zeolite beta, a crystal size of less than one micron and a water adsorption capacity of less than 0.01 g/g of molecular sieve.

2. A crystalline silicate molecular sieve having the topology of zeolite beta, a crystal size of less than one micron and a water adsorption capacity of less than 0.01 g/g of molecular sieve.

3. A method of preparing a crystalline material having the topology of zeolite beta comprising impregnating a silica-containing mesoporous material with an aqueous solution of tetraethylammonium cation in an amount sufficient to form a crystalline product having the topology of zeolite beta, and wherein the water to mesoporous material molar ratio is from about 0.5 to about 2, and subjecting the impregnated mesoporous material to crystals of a material having the topology of zeolite beta.

4. The method of claim 3 wherein the mesoporous material is an all-silica material.

5. The method claim 3 wherein the mesoporous material comprises, in addition to silica, an oxide selected from the group consisting of aluminum oxide, boron oxide, titanium oxide, vanadium oxide, zirconium oxide, zinc oxide and mixtures thereof.

6. The method of claim 4 wherein the mesoporous material is MCM-41 or MCM-48.

7. The method of claim 5 wherein the mesoporous material is MCM-41 or MCM-48.

* * * * *